(12) United States Patent
Vason et al.

(10) Patent No.: US 9,347,028 B2
(45) Date of Patent: May 24, 2016

(54) PROCESS FOR EXTRACTING UNWANTED ACIDIC COMPOUNDS FROM A DRINKABLE LIQUID

(71) Applicant: ENOLOGICA VASON S.p.A., San Pietro in Cariano (VR) (IT)

(72) Inventors: Albano Vason, San Pietro in Cariano (IT); Enrico Bocca, Sant'Ambrogio di Valpolicella (IT)

(73) Assignee: ENOLOGICA VASON S.P.A., San Pietro In Cariano (VR) (IT)

( * ) Notice: Subject to any disclaimer, the term of this patent is extended or adjusted under 35 U.S.C. 154(b) by 128 days.

(21) Appl. No.: 14/073,917

(22) Filed: Nov. 7, 2013

(65) Prior Publication Data

US 2014/0127366 A1    May 8, 2014

(30) Foreign Application Priority Data

Nov. 7, 2012  (IT) .............................. PD2012A0332

(51) Int. Cl.
*C12H 1/16* (2006.01)
*C12G 3/00* (2006.01)
(Continued)

(52) U.S. Cl.
CPC ... *C12H 1/16* (2013.01); *A23L 2/02* (2013.01); *A23L 2/085* (2013.01); *A23L 2/087* (2013.01); *A23L 2/70* (2013.01); *A23L 2/74* (2013.01); *B01D 61/58* (2013.01); *C07C 51/42* (2013.01); *C12G 3/00* (2013.01); *C12G 3/08* (2013.01); *C12G 3/085* (2013.01); *B01D 61/025* (2013.01); *B01D 61/44* (2013.01); *B01D 2317/025* (2013.01); *B01D 2317/027* (2013.01)

(58) Field of Classification Search
CPC ............ C12H 1/16; C07C 51/42; C12G 3/00; C12G 3/08; C12G 3/85; A23L 2/02; A23L 2/085; A23L 2/087; A23L 2/70; A23L 2/74; B01D 61/58

See application file for complete search history.

(56) References Cited

U.S. PATENT DOCUMENTS

| 3,865,961 A | 2/1975 | Wucherpfennig et al. |
| 4,015,020 A | 3/1977 | Nagasawa et al. |

(Continued)

FOREIGN PATENT DOCUMENTS

| EP | 0460339 | 9/1991 |
| EP | 1 146 115 | 5/2005 |

(Continued)

*Primary Examiner* — Anthony Weier
(74) *Attorney, Agent, or Firm* — Mark M. Friedman (57) ABSTRACT

Process for extracting unwanted acidic compounds from a drinkable liquid which includes:
  arranging, in a first tank (2), a liquid (L) has at least one unwanted acidic compound;
  conveying the liquid (L) to a membrane separation unit (3);
  separating, in the membrane unit (3), the liquid (L) into a retentate (R) and a permeate (P) mainly containing the unwanted acidic compound;
  adjusting the conductivity of the permeate (P) at a minimum threshold value greater than 200 μS susceptible to dissociate at least a fraction of the unwanted acidic compound into corresponding ions;
  flowing the permeate (P) through an electrodialysis unit (6), extracting at least part of said ions, to obtain one concentrate (C), containing the aforesaid ions, and one deacidified permeate (Pd) substantially without such ions;
  mixing the deacidified permeate (Pd) with the retentate (R) to obtain the deacidified final drinkable liquid.

11 Claims, 3 Drawing Sheets

(51) Int. Cl.
  *C12G 3/08* (2006.01)
  *A23L 2/02* (2006.01)
  *A23L 2/08* (2006.01)
  *C07C 51/42* (2006.01)
  *A23L 2/70* (2006.01)
  *A23L 2/74* (2006.01)
  B01D 61/58 (2006.01)
  *B01D 61/02* (2006.01)
  *B01D 61/44* (2006.01)

(56) References Cited

U.S. PATENT DOCUMENTS

| | | | | |
|---|---|---|---|---|
| 4,855,056 A | * | 8/1989 | Harju | A23C 9/144 |
| | | | | 210/638 |
| 4,885,247 A | * | 12/1989 | Datta | B01D 61/44 |
| | | | | 204/527 |
| 5,143,834 A | | 9/1992 | Glassner | |
| 5,260,080 A | * | 11/1993 | Noel | A23C 9/1422 |
| | | | | 426/239 |
| 5,681,728 A | * | 10/1997 | Miao | C12P 7/56 |
| | | | | 204/519 |
| 6,284,116 B1 | | 9/2001 | Wiese et al. | |
| 6,440,222 B1 | * | 8/2002 | Donovan | B01D 61/142 |
| | | | | 127/43 |
| 7,651,616 B2 | | 1/2010 | Tudhope | |
| 2004/0067280 A1 | | 4/2004 | Bonnet et al. | |
| 2007/0248729 A1 | | 10/2007 | Sandu | |
| 2010/0092628 A1 | * | 4/2010 | Neves Correia De Pinto | A23L 2/085 |
| | | | | 426/239 |

FOREIGN PATENT DOCUMENTS

| | | |
|---|---|---|
| GB | 1 416 010 | 12/1975 |
| JP | S61 271296 | 1/1986 |
| PT | 105008 | 1/2012 |
| WO | 03074650 | 9/2003 |

* cited by examiner

PROCESS FOR EXTRACTING UNWANTED ACIDIC COMPOUNDS FROM A DRINKABLE LIQUID

FIELD OF APPLICATION

The present invention regards a process and a plant for extracting unwanted acidic compounds from a drinkable liquid and in particular from a wine.

The present invention is intended to be advantageously employed in the field of alcoholic and non-alcoholic beverages for removing one or more unwanted acidic compounds present in unwanted concentrations in a beverage. In particular, the present invention is intended to be employed in the winemaking field in order to reduce the concentration of compounds that determine the volatile acidity of the wine, in order to improve the organoleptic characteristics of the latter.

STATE OF THE ART

The problem of extracting unwanted acidic compounds from drinkable liquids has been confronted in many fields of the art and particularly in the field of alcoholic and non-alcoholic beverages, such as fruit juices and wine.

In particular, in the wine industry, there is the considerable problem of extracting acidic compounds present in solution in the wine, such as ethyl acetate, acetic acid and other homologous carboxylic acids, which are formed during fermentation or in subsequent stages of the vinification process and which determine the so-called volatile acidity of the wine.

Excess volatile acidity in a wine indeed negatively affects the organoleptic characteristics of the same, giving the wine a rather unpleasant taste and bouquet. Such alteration in particular is accentuated by the presence of ethyl acetate in excessive concentrations.

A simple technique, frequently used by wine producers in order to remedy the aforesaid problem, consists of mixing the wine having an excessive volatile acidity with a wine having low volatile acidity, in order to obtain a final product with an overall volatile acidity lower than a limit value considered acceptable.

The outcome of the aforesaid mixing is however unpredictable, and the wine thus obtained could have unsatisfactory organoleptic properties.

Over the years, therefore, numerous processes and plants have been designed adapted to be employed for extracting the unwanted acidic compounds from wines having an excessive volatile acidity, in order to improve the sensory characteristics and the overall quality of such wines.

Such processes generally provide for the separation of the unwanted acidic compounds from the wine through the use of membranes, obtained with materials and morphology such to facilitate the extraction, as selective as possible, of specific predefined compounds.

Known, for example from the patent application WO 03/074650, are a plant and a process adapted to be employed for reducing the volatile acidity of a wine.

The process described therein comprises a first step of separating the wine to be treated into a first concentrate and a first permeate, in which the unwanted acidic compounds are contained, and a second step of separating the first permeate in turn into a second concentrate, in which the aforesaid unwanted compounds are contained, and a second permeate which comprises the solvent and the solutes to be preserved in the wine. The second permeate thus obtained is recombined with the first concentrate to obtain a wine having reduced volatile acidity.

The first and the second separation step are obtained through respective membranes which, depending on the size of the molecules of the acidic compounds that one wishes to remove from the wine, can be reverse osmosis membranes, nanofiltration membranes or ultrafiltration membranes.

The patent application WO 03/074650 also teaches to neutralize the first permeate by introducing an additive in the latter, such additive having a high pH value and can for example be calcium carbonate.

The process described briefly above has nevertheless proven in practice to not be free of drawbacks.

The main drawback consists of the poor efficiency of such process, which is not sufficiently functional, given that it is particularly difficult to remove high percentages of unwanted acidic compounds through simple filtration.

In addition, the additives with high pH value that are added into the first permeate in order to neutralize it, such as in particular calcium carbonate, may remain in the second permeate and hence be present in the wine at the end of the treatment. Such additives can negatively affect the organoleptic properties of the treated wine and can give rise to precipitates.

Also known are processes and plants for reducing the volatile acidity of wines which use ion exchange resins, i.e. in particular anionic resins especially suitable for removing acetic acid and/or ethyl acetate, such as is described for example in the U.S. Pat. No. 5,480,665. More in detail, in the abovementioned processes the wine to be treated, or a permeate extracted therefrom, is made to cyclically flow through the ion exchange resins, in order to facilitate the selective removal from the wine of the ions responsible for the volatile acidity, in such a manner reducing the acidity of the wine.

The latter processes and plants are nevertheless hard to manage. In particular, it is particularly difficult to accurately select the acidic compounds that are removed through the ion exchange resins, with the risk that, together with the undesired compounds, compounds are also extracted that preferably should remain in the wine, to the detriment therefore of the sensory quality, i.e. of the organoleptic properties, of the treated wine. Furthermore, the use of anionic resins can cause the transfer by the same of bad-smelling substances, which negatively affect the quality of the treated product, involving a consequent deterioration thereof.

Other processes and plants of known type for the extraction of acidic compounds from the wine revealing the same abovementioned drawbacks are further described in the patents EP 1146115 and U.S. Pat. No. 7,651,616.

PRESENTATION OF THE INVENTION

In this situation, the problem underlying the present invention is to eliminate the drawbacks of the abovementioned prior art, by providing a process for extracting unwanted acidic compounds from a drinkable liquid and in particular from a wine or from a grape must, which is highly selective, allowing the extraction of predefined unwanted acidic compounds from the drinkable liquid to be treated, and in particular from the wine. Another object of the present finding is to provide a process for extracting unwanted acidic compounds from a drinkable liquid and in particular from a wine or from a grape must that is easy to manage.

A further object of the present finding is to provide a process and a plant for extracting unwanted acidic compounds from a drinkable liquid and in particular from a wine or from a grape must that allows improving the efficiency of the removal of the aforesaid unwanted acidic compounds.

Another object of the present finding is to provide a process and a plant for extracting unwanted acidic compounds from a drinkable liquid and in particular from a wine or from a grape must which do not negatively affect the organoleptic properties of the liquid at the end of the treatment.

A further object of the present finding is to provide a plant for extracting unwanted acidic compounds from a drinkable liquid and in particular from a wine or from a grape must that is structurally simple and entirely reliable in operation.

BRIEF DESCRIPTION OF THE DRAWINGS

The technical characteristics of the finding, according to the aforesaid objects, can be clearly seen in the contents of the below-reported claims and the advantages thereof will be more evident in the following detailed description, made with reference to the enclosed drawings, which represent a merely exemplifying and non-limiting embodiment of the invention, in which:

DETAILED DESCRIPTION OF A PREFERRED EMBODIMENT

With reference to the enclosed figures, the reference number 1 indicates the plant for extracting unwanted acidic compounds from thinkable liquids, object of the present invention, in its entirety.

Such plant 1 is intended to be used in general in the food industry, and particularly in the winemaking industry, in order to treat numerous liquid types. Hereinbelow, in order to simplify the description, reference will only be made to the case of an enological product, such as a wine or a grape must, from which in particular acetic acid is extracted in order to reduce the volatile acidity of the wine itself; nevertheless, it is intended that the use of such plant is also associated with other drinkable liquids for extracting acetic acid or other unwanted acidic compounds, without departing from the protective scope of the present patent.

In addition, where reference is made to wine in the present document, it is intended to be referred to an enological product in general, such as a grape must.

The plant 1, comprises a first tank 2 for containing a drinkable liquid to be treated L containing one or more unwanted acidic compounds, in solute form.

Preferably, the plant 1 is optimized for extracting a specific and predetermined unwanted acidic compound.

In particular, the unwanted acidic compound can already be present in the drinkable liquid to be treated L, or it can be an acidic compound derived from a different unwanted non-acidic compound present in the drinkable liquid to be treated L. For example, the unwanted acidic compound extracted from the drinkable liquid L can be acetic acid deriving from the ethyl acetate by means of a hydrolysis reaction, through which the ethyl acetate is transformed into ethanol and acetic acid.

Therefore, by means of the plant 1 and the process according to the present invention, it is possible to reduce the concentration also of unwanted non-acidic compounds present in the drinkable liquid to be treated L, such as ethyl acetate.

For such purpose, it is indeed sufficient to remove, from the drinkable liquid to be treated L, an acidic compound obtained from the transformation (spontaneous or deliberately induced) of an unwanted non-acidic compound present in the drinkable liquid to be treated L.

The plant 1 also comprises a membrane separation unit 3 adapted for separating the drinkable liquid to be treated L into a retentate R and a permeate P.

Downstream of the membrane separation unit 3, the acidic compound that one wishes to remove from the drinkable liquid L is mainly contained in the permeate P. The retentate R contains most of the solutes that preferably must be maintained in the drinkable liquid, i.e. in particular in the case of a wine those compounds that confer structure, taste, aroma and color to the wine, defining its organoleptic properties. As will be better specified hereinbelow, the retentate R is intended to be recombined with the deacidified permeate at the end of the treatment to obtain the deacidified drinkable liquid.

The membrane separation unit 3 comprises one or more membranes which, as a function of the compound that one wishes to extract from the liquid to be treated and in particular as a function of the size of the molecules of such compound, can for example be nanofiltration membranes, ultrafiltration membranes, or reverse osmosis membranes.

In accordance with a preferred embodiment of the plant 1 according to the present invention, the membrane separation unit 3 is a reverse osmosis unit, and the membrane (or membranes) provided therein is a reverse osmosis membrane.

Indeed, such membrane ensures an optimal selectivity towards the unwanted acidic compounds, preventing compounds from being transferred into the permeate P which must instead be preferably retained in the retentate R, in order to remain in the drinkable liquid at the end of the treatment, as will be clarified hereinbelow.

The drinkable liquid obtained at the end of the treatment will only have a low concentration of the unwanted acidic compounds, whereas it will keep its remaining composition characteristics substantially unaltered.

In particular, the type of reverse osmosis membrane selected for being employed in the separation unit 3 of the plant 1 determines which unwanted compound is transferred to the permeate P, i.e. it determines the selectivity of the extraction process obtained through the plant 1.

For example, if the drinkable liquid is a wine and the unwanted acidic compound to be extracted is acetic acid, the use of a reverse osmosis membrane in the separation unit 3 ensures that substantially only the acetic acid is transferred into the permeate P, whereas other acids, even if they also have molecules of limited size, such as lactic acid, and which must preferably be maintained in the wine at the end of the treatment, are retained in the retentate R.

The reverse osmosis membrane leads to a greater rejection of acetic acid, with respect for example to a nanofiltration membrane, retaining in the retentate R even up to 20-25% acetic acid—to the detriment of the efficiency of the overall acetic acid extraction process. Nevertheless, it is still preferable to use such membrane due to its optimal selectivity, with the above-specified advantages that derive therefrom.

A reverse osmosis membrane that can be advantageously used in the plant 1 in accordance with the present invention is for example a thin-film membrane (TFM) having an average rejection of 99% over 2000 ppm of NaCl at 25° C. and at 2,930 KPa.

The plant 1 comprises first circulation means 4 adapted for receiving the drinkable liquid to be treated L from the first tank 2—and for such purpose in particular such means 4 are connected in inlet to the first tank 2—and for conveying such drinkable liquid through the membrane separation unit 3—and for such purpose in particular such means 4 are connected in outlet to the separation unit 3. In such a manner, the drinkable liquid is separated in the separation unit 3 into the retentate R and the permeate P.

Advantageously, the first circulation means 4 comprise a first duct 4' for transporting the drinkable liquid to be treated L from the first tank 2 to the membrane separation unit 3 and a pump 4" placed to intercept the first duct 4' and adapted to send the liquid to be treated L under pressure to the separation unit.

Preferably, when the membrane separation unit 3 is a reverse osmosis unit, the pump 4" is adapted to send the liquid to be treated L to the separation unit 3 with a pressure comprised between 40 and 80 bars.

In accordance with the idea underlying the present invention, the plant 1 also comprises a dosing unit 5 for at least one neutralization compound N, such dosing unit 5 adapted, if necessary, for dosing and releasing into the permeate P a dose of one or more neutralization compounds N adapted to react with the compound or with the unwanted acidic compounds to form a corresponding salt of the unwanted acidic compound and thus obtain a permeate P in neutralized form. Preferably, such permeate P in neutralized form has a desired and predefined pH value and has a conductivity value greater than 200 μS and preferably equal to at least 500 μS, such minimum value of conductivity being susceptible to dissociate at least a fraction of the unwanted acidic compound (or of the unwanted acidic compounds) into corresponding ions.

Indeed, the degree of dissociation of the unwanted acidic compounds into ions is connected to the conductivity value of the permeate P, such that greater values of conductivity correspond with greater degrees of dissociation of the unwanted acidic compounds into ions. In particular, a minimum value of the conductivity of the permeate P greater than 200 μS, and preferably equal to at least 500 μS, has proven suitable for ensuring a degree of dissociation of the unwanted acidic compound into ions (or of the unwanted acidic compounds into ions) that is sufficient for allowing the removal of at least a part of the above mentioned ions by means of electrodialysis, as is better explained hereinbelow.

The addition of one or more neutralization compounds N to the permeate P if necessary, i.e. if the conductivity of the permeate P is less than 200 μS, thus allows increasing the value of the conductivity of the permeate P, with the formation of corresponding salts of the unwanted acidic compound, such salts present in solution in the permeate P in dissociated form, i.e. in the form of ions.

Advantageously, the plant 1 can comprise a first conductivity meter 10 for measuring the value of conductivity of the permeate P upstream of the dosage unit 5, such that, on the basis of the value of conductivity of the permeate P detected, it will be possible to establish if a dose of one or more neutralization compounds N into the permeate P is to be released or not.

In particular, the neutralization compound N intended to be added if necessary to the permeate P comprises one or more bases, one or more salts or a mixture of one or more bases with one or more salts.

Advantageously, the neutralization compound N employed in the plant 1 and in the process for extracting unwanted acidic compounds from a drinkable liquid according to the present invention comprises one or more bases, and preferably a single base, as better specified hereinbelow; nevertheless, it is intended that the same neutralization compound N can comprise one or more salts or a mixture of one or more bases with one or more salts, without departing from the protective scope defined by the present patent.

The plant 1 also comprises an electrodialysis unit 6, which is adapted for receiving the permeate P, possibly neutralized, having a conductivity greater than 200 μS and preferably equal to at least 500 μS and containing at least a fraction of the unwanted acidic compound dissociated into corresponding ions. Through the electrodialysis unit 6, the ions derived from the unwanted acidic compound, i.e. the ions derived from the dissociation of the unwanted acidic compound or from the dissociation of its corresponding salt being formed downstream of the dosing unit 5 (via reaction of the neutralization compound N with the unwanted acidic compound) are extracted from the permeate P, as is better specified hereinbelow. The electrodialysis unit 6 is therefore adapted for separating the permeate P into a concentrate C, containing the ions derived from the unwanted acidic compound, and a deacidified permeate Pd, substantially without the aforesaid ions, from which the anions have therefore been extracted (especially the acetate ion) along with the cations, i.e. in particular the proton $H^+$, or the cations used for obtaining the preceding neutralization step.

More in detail, in the electrodialysis unit 6, the ions derived from the dissociation of the unwanted acidic compound or from the dissociation of the salts being formed downstream of the dosing unit 5, present in the permeate P, are transferred to an extractor liquid E, which, enriched with the aforesaid ions, forms the concentrate C, as will be better explained hereinbelow.

The permeate P, downstream of the electrodialysis unit 6, and therefore following the removal of the above mentioned ions, has a value of conductivity less than the value of conductivity upstream of the electrodialysis unit 6.

In particular, the value of conductivity of the permeate P exiting the electrodialysis unit 6 is bound to the concentration of the residual unwanted acidic compound present therein, so that obtaining a permeate P downstream of the electrodialysis unit 6 having a conductivity less than a preset threshold value ensures a residual concentration of the unwanted acidic compound less than a threshold concentration also preset. To the aim hence to obtain a permeate P containing the unwanted acidic compound in a concentration less than a threshold value considered acceptable, it is sufficient to have the permeate P undergoing electrodialysis until the conductivity value of the latter exiting the electrodialysis unit 6 is less than a preset threshold value of conductivity.

For instance, reaching a value of conductivity of the permeate P exiting the electrodialysis unit 6 less than 100 μS, and in particular of about 80 μS, ensures a concentration of acetic acid in the permeate P less than 0.15 g/l, and in particular less than 0.10 g/l.

Advantageously, the plant 1 can comprise a second conductivity meter 11 for measuring the value of conductivity of the permeate P downstream of the eletrodialysis unit 6.

Also provided are second circulation means 7 to circulate the permeate P from the membrane separation unit 3 through the dosing unit 5 and through the electrodialysis unit 6.

Figure 1:
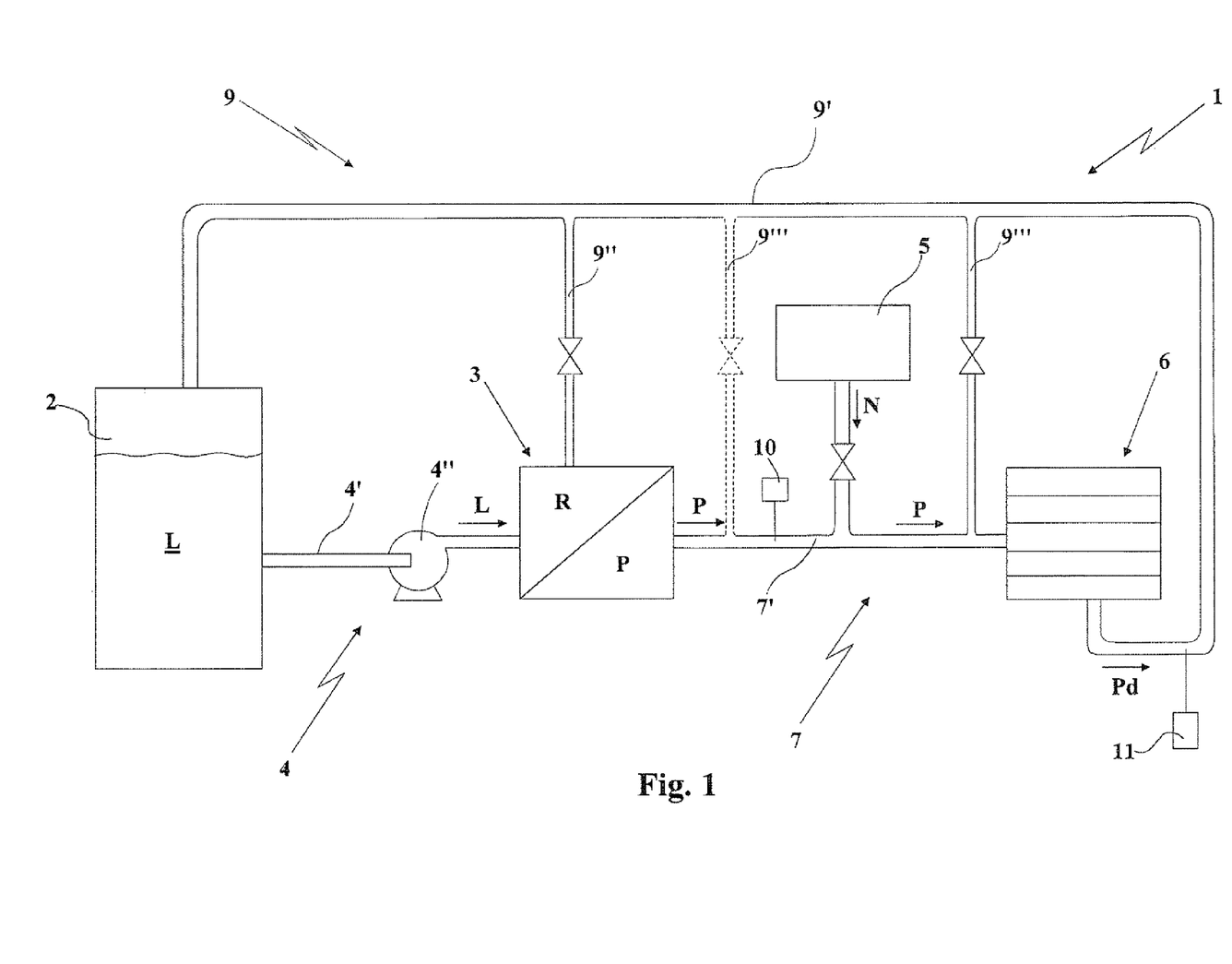
FIG. 1 shows a functional logic scheme of the plant for extracting unwanted acidic compounds from a drinkable liquid, in particular from a wine, object of the present invention, in accordance with a first embodiment.

In accordance with a first embodiment of the plant according to the present invention, illustrated in FIG. 1, the second circulation means 7 comprise a second duct 7' connected with the separation unit 3 in inlet, for receiving the permeate P therefrom, connected with the dosing unit 5, for receiving if necessary the neutralization compound therefrom and connected in outlet, downstream of the dosing unit 5, with the electrodialysis unit for transferring the neutralized permeate Pn to the latter. Advantageously, in order to allow the selective introduction of the neutralization compound N into the permeate P, the second circulation means 7 comprise a valve placed to intercept a duct for supplying the neutralization compound N to the second duct 7', as illustrated in FIG. 1.

Figure 2:
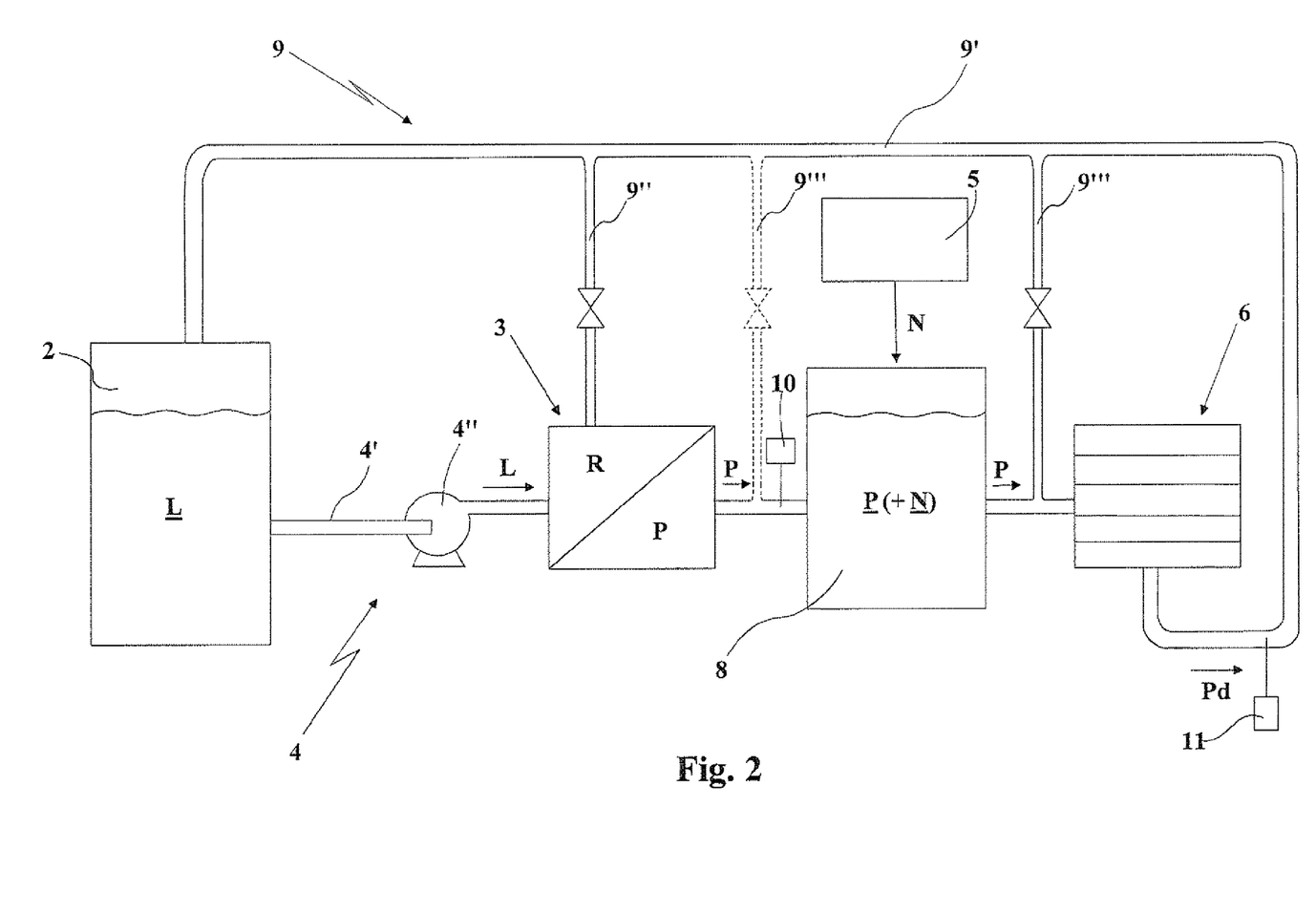
FIG. 2 shows a functional logic scheme of the plant for extracting unwanted acidic compounds from a drinkable liquid, in particular from a wine, object of the present invention, in accordance with a second embodiment.

Otherwise, in accordance with a further embodiment of the plant 1 according to the present invention, illustrated in FIG. 2, if the neutralization of the permeate P is carried out in batches, as is better explained hereinbelow, the second circulation means 7 can comprise a second tank 8 for containing the permeate P. The dosing unit 5 in such case is adapted for dosing and releasing doses of the neutralization compound N in the permeate contained in the second tank 8.

Advantageously, the plant 1 also comprises recirculation means 9, which comprise a third duct 9' which hydraulically connects the electrodialysis unit 6 with the first tank 2 for transporting the deacidified permeate Pd from the electrodialysis unit 6 to the first tank 2 and reintroducing the deacidified permeate Pd in the liquid to be treated. The recirculation means 9 can also comprise a fourth duct 9" which hydraulically connects the membrane separation unit 3 with the first tank 2 (or with the third duct 9') for transporting the retentate R from the separation unit 3 to the first tank 2 (or to the third duct 9') and reintroducing the retentate R in the liquid to be treated, if the retentate R is also recirculated in the plant 1.

The recirculation means 9 can also comprise at least a fifth duct 9''' which hydraulically connects the electrodialysis unit 6 with the second circulation means 7e, in particular, with the second duct 7' upstream and/or downstream of the dosing unit 5, for allowing the recirculation of the deacidified permeate Pd through the electrodialysis unit 6 till reaching a desired value of conductivity of the deacidified permeate Pd.

The plant 1 also comprises means for recombining the retentate R with the deacidified permeate Pd to obtain the deacidified drinkable liquid.

Indeed, when the value of conductivity of the deacidified permeate Pd is less than a preset threshold value, that is the concentration of the unwanted acidic compound in the deacidified permeate Pd is less than a pre-established maximum limit value, the retentate R is mixed with the deacidified permeate Pd to obtain the deacidified drinkable liquid.

In particular, the recombining means can be defined by the third duct 9' for reintroducing the deacidified permeate Pd in the first tank 2, by the fourth duct 9" for pouring the retentate R into the first tank 2 or into the third duct 9' and by the first tank 2 itself, or they can be defined by dedicated ducts not illustrated in the enclosed drawings.

Also forming the object of the present invention is a process for extracting unwanted acidic compounds from a drinkable liquid, and in particular from a wine, intended to be achieved in particular through a plant 1 of the above-described type; the same reference numbers will be maintained hereinbelow.

Below, reference will be made to the use of the process according to the present invention for extracting a single unwanted acidic compound; nevertheless, it is intended that the process according to the present invention can also be optimized for simultaneously extracting multiple unwanted acidic compounds.

In addition, by means of the present process, simultaneously with the unwanted acidic compound (or unwanted acidic compounds), different compounds, even non-acidic ones, can also be removed.

The process in accordance with the present invention comprises a first operative step of arranging, in the first tank 2, a drinkable liquid to be treated L, comprising an unwanted acidic compound, in an initial concentration.

Also provided is the conveying of the drinkable liquid to be treated L to the membrane separation unit 3 and the separation, in the latter, of the drinkable liquid to be treated L into a retentate R and a permeate P, with the unwanted acidic compound mainly contained in the permeate P, as specified above.

Preferably the separation is carried out through reverse osmosis, which ensures an optimal selectivity of the compounds which can cross through the reverse osmosis membrane and are then transferred into the permeate P.

The adjustment of the conductivity of the permeate P is then provided at a minimum threshold value greater than 200 $\mu S$ and preferably equal to at least 500 $\mu S$, susceptible to dissociate at least a fraction of the unwanted acidic compound into corresponding ions. Advantageously, the adjustment of the conductivity of the permeate P comprises a first step of measuring the conductivity of the permeate P, a first step of confronting the measured value of conductivity with the minimum threshold value and a step of introduction in the permeate P of a correspondent dose of one or more neutralization compounds N susceptible to bring the conductivity of the permeate P to a value greater than the aforesaid minimum threshold value.

The aforesaid minimum value of conductivity of the permeate P allows in fact closing the electric circuit inside the electrodialysis unit 6 and hence ensures that the electrodialysis can be conducted in an effective manner on the permeate P itself.

If the value of the conductivity of the permeate P exiting from the membrane separation unit 3 is greater than 200 $\mu S$, it is not necessary to intervene on the permeate P itself, which is thus adapted to be directly sent to the electrodialysis unit 6. If, however, the value of the conductivity of the permeate P exiting from the membrane separation unit 3 is less than or equal to 200 $\mu S$, the adjustment of the conductivity of the permeate P comprises the aforesaid operative step of introducing in the permeate P one or more neutralization compounds N (preferably of only one neutralization compound N). The neutralization compound N added to the permeate P reacts with the unwanted acidic compound contained in the permeate P to form a respective salt therewith.

Of course, it will be possible to provide for the operative step of neutralization even in the case in which the conductivity of the permeate P exiting from the membrane separation unit 3 is greater than 200 $\mu S$, in order for example to allow a quicker removal of the unwanted acidic compound by means of electrodialysis.

As specified above, the neutralization compound N in particular comprises a base, a salt or a mixture of a base and a salt. Preferably, the neutralization compound comprises a base.

The operative neutralization step leads to the formation of a permeate P in neutralized form advantageously having a pH comprised between 4 and 8, and preferably having a pH equal to about 5.

In particular, the neutralization of the acidity of the permeate P can occur continuously. In such case, the addition if necessary of the neutralization compound N to the permeate P can be carried out by introducing such compound N in the permeate P until the latter flows from the separation unit 3 towards the electrodialysis unit 6, for example through the second duct 7'. Otherwise, the neutralization of the acidity of the permeate P can occur in batches. In the latter case, the permeate P exiting from the membrane separation unit 3 is collected in the second tank 8 and the neutralization compound N is added if necessary to the permeate P in the second tank 8.

The process according to the present invention also comprises subsequently flowing the permeate P through the electrodialysis unit 6, with the extraction from the permeate P of at least a part of the ions deriving from the dissociation of the aforesaid unwanted acidic compound or deriving from the dissociation of the corresponding salt to obtain at least one concentrate C, containing the aforesaid ions, and at least one deacidified permeate Pd, substantially free of the aforesaid ions.

Figure 3:
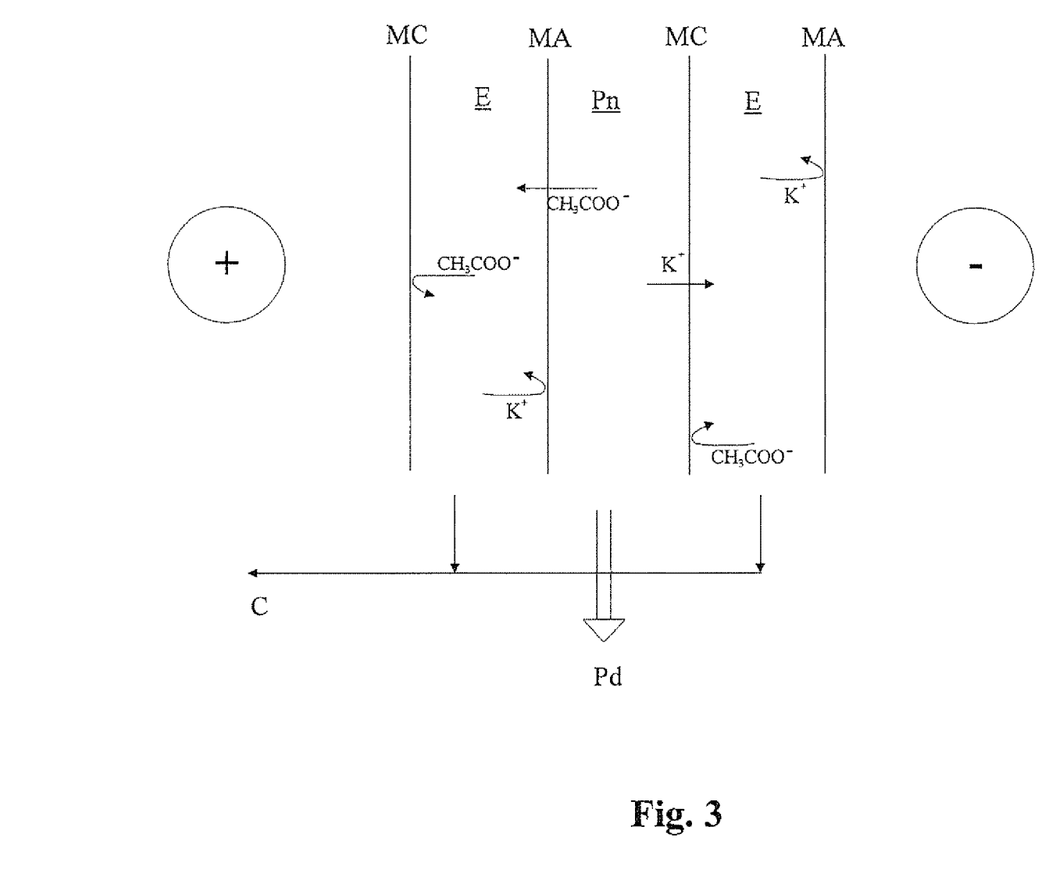
FIG. 3 shows a schematic representation of the operating principle of the electrodialysis unit provided in the plant, object of the present invention.

More in detail, the electrodialysis unit 6 comprises, in a per se known manner and therefore not discussed in detail herein, a plurality of anionic semipermeable membranes MA (permeable only to anions) and cathodic semipermeable membranes MC (permeable only to cations) arranged alternated. The permeate P and an extractor liquid E are made to flow between the membranes, as is schematically indicated in FIG. 3, and are subjected to the action of an electric field created by two electrodes. The positive and negative ions deriving from the dissociation of the unwanted acidic compound or of the corresponding salt present in solution in the permeate P migrate, under the action of the electric field, towards the electrode with charge opposite thereto, being able to respectively cross the cationic and anionic membrane, and being instead respectively repelled by the anionic and cationic membrane. In such a manner, there is the separation of the solute (the ions deriving from the unwanted acidic compound) from the solvent and the concentration of the first in the compartments where the extractor liquid E flows, and of the deacidified permeate Pd in the remaining compartments.

The extractor liquid E enriched with the ions deriving from the unwanted acidic compound therefore forms the abovementioned concentrate C.

Schematically indicated in FIG. 3 is the extraction of the cations and anions deriving from the dissociation of an acetic acid salt, or in particular the potassium acetate salt, from a neutralized permeate $P_n$ obtained through the addition in the permeate P of for example potassium hydroxide as neutralization compound N, as will be better explained hereinbelow.

The conductivity value greater than 200 μS of the permeate P is thus the minimum value that ensures the presence of a quantity of ions deriving from the dissociation of the unwanted acidic compound that is sufficient to allow executing the electrodialysis on the permeate P, without it being necessary to excessively increase the power of the electrodialysis and hence cause high wear of the membranes of the electrodialysis unit 6. Only with a conductivity value of the permeate P greater than 200 μS, therefore, the unwanted acidic compound can be present in ionic form in the permeate in quantities sufficient to allow the extraction thereof by means of electrodialysis. Indeed, if the permeate P has a conductivity value less than or equal to 200 μS, the electrodialysis could not be effectively conducted on the permeate P.

For such purpose, before the adjustment of the conductivity of the permeate P, a further operative step can be advantageously provided for determining the conductivity of the permeate P, in order to evaluate the need (or lack of need) to proceed with the step of neutralizing the permeate P in order to increase the conductivity of the permeate P. Advantageously, the step of flowing the permeate P through the electrodialysis unit 6 envisages a second step of measuring the conductivity of the permeate P exiting the electrodialysis unit 6, a second step of confronting the measured conductivity value with a reference conductivity value of the permeate P to which a threshold value of the acidity (i.e. of the concentration of the unwanted acidic compound) corresponds, and a step of recirculating the permeate P in the electrodyalisis unit 6 until, in the aforesaid step of confronting, the measured value is lower than the reference value. In particular the step of recirculating can be performed by flowing the deacidified permeate P through the fifth duct 9''' which hydraulically connects the electrodialysis unit 6 with the second duct 7' upstream and/or downstream of the dosing unit 5.

Given that the conductivity of the permeate P depends on the concentration of the unwanted acidic compound in the permeate P itself, such that low concentrations of the unwanted acidic compound in the permeate P correspond with low conductivity values, as the extraction process continues, i.e. following the repetition for one or more cycles of the aforesaid operative steps, the operative step of neutralizing the permeate P might be necessary in order to ensure the attainment of the minimum value of conductivity of the permeate P required for the effective execution of the electrodialysis even at low concentrations of the unwanted acidic compound.

The possible step for neutralizing the permeate P allows increasing the conductivity of the permeate through the acquisition of a net charge by the ion of the unwanted acidic compound, which forms a respective salt with the neutralization compound N, or preferably with the base.

With particular reference to the process of extraction of acetic acid from a wine, the neutralization of the permeate with the neutralization compound N determines the acquisition of a net charge by the acetate ion.

If the process according to the present invention is employed for reducing the volatile acidity of a wine, and thus the drinkable liquid to be treated L is wine, and the neutralization compound N comprises a base, such base added to the permeate P in the step of neutralizing the permeate can advantageously be sodium hydroxide (NaOH) or, preferably, potassium hydroxide (KOH).

Potassium is in fact an element naturally present in wine. Therefore, if in the step of extracting the unwanted acidic compound through electrodialysis, there is a slight leakage of potassium ions K⁺ into the deacidified permeate Pd, their presence in the wine at the end of the treatment, obtained from the mixing of the retentate with the deacidified permeate Pd, would in any case not negatively affect the quality of the wine itself.

In particular, in such case, the reaction of neutralization of the acetic acid contained in the permeate P by the potassium hydroxide is the following:

$$CH_3COOH + KOH \rightarrow CH_3COOK + H_2O$$

The potassium acetate thus formed is present in solution in the neutralized permeate Pn in ionic form, i.e. split into acetate ion $CH_3COO^-$ and potassium ion $K^+$.

If the process according to the present invention is employed for reducing the volatile acidity of a wine, and thus the drinkable liquid to be treated L is wine, and the neutralization compound N comprises a salt, such salt added to the permeate P in the step of neutralizing the permeate can be for example potassium sulfate ($K_2SO_4$) or potassium phosphate ($K_3PO_4$). Indeed, both such salts are provided have good compatibility with wine and the products of the neutralization reaction that must remain in the wine at the end of the treatment do not negatively affect, in a significant manner, the organoleptic properties of the treated wine.

The neutralization compound N is added to the permeate P in a quantity such to ensure the removal, as complete as possible, of the unwanted acidic compound during the electrodialysis step.

For such purpose, the process preferably comprises, before the addition of the neutralization compound N to the permeate P, the further operative steps of determining the concentration of the unwanted acidic compound in the drinkable liquid to be treated L or in the permeate P and consequently defining the dose of the neutralization compound N that must be added to the permeate P in order to allow the neutralization of the unwanted acidic compound.

In particular, the determination of the concentration of the unwanted acidic compound can for example be carried out through an enzymatic analysis of the permeate P or by measuring the conductivity of the permeate P.

The dose of the neutralization compound N added to the permeate P can be equal to the dose stoichiometrically necessary for reacting with the unwanted acidic compound present in the previous determined concentration in the permeate P. In particular, when the process is employed for extracting acetic acid from a wine and the neutralization compound added to the permeate P is potassium hydroxide, the potassium hydroxide can be added to the permeate P in a 1:1 molar ratio with respect to the acetic acid.

Nevertheless, in order to increase the extraction efficiency of the electrodialysis, or in order to facilitate the removal, as complete as possible, of the unwanted acidic compound from the permeate P, the dose of the neutralization compound N added to the permeate P is preferably greater than the dose stoichiometrically necessary for reacting with the unwanted acidic compound present in the previously determined concentration in the permeate P.

Indeed, the decrease of the concentration of the ionic species present in the permeate P, due to the progressive extraction of the ionic species themselves from the permeate P through electrodialysis, leads to a decrease of the conductivity of the permeate itself and hence it will be more difficult to extract the residue ionic species through electrodialysis. The presence of an excess quantity of neutralization compound N, present in ionic form in the permeate P, allows maintaining high conductivity in the permeate P and thus allows the extraction of the ionic species from the latter through electrodialysis, even at low ion concentrations of the unwanted compound. In such a manner, it is possible to continue extracting the ions of the unwanted compound through electrodialysis even when the concentration of the latter is quite low, hence allowing the substantially complete extraction of the ions of the unwanted compound.

In particular, when the process is employed for extracting acetic acid from a wine and the neutralization compound N added to the permeate P is potassium hydroxide, the stoichiometric ratio between the acetic acid present in the permeate P and the potassium hydroxide added to the permeate P is preferably 1:1.5.

The quantity of potassium hydroxide thus introduced in the permeate P is sufficiently high to ensure the maintenance of good conductivity of the neutralized permeate P and hence to facilitate the extraction, as complete as possible, of the ions of the unwanted compound. Such quantity of potassium hydroxide is at the same time sufficiently limited so as to prevent leakage from occurring through the deacidified permeate Pd of unwanted quantities, or quantities considered excessive, of potassium, which could negatively affect the organoleptic properties of the wine at the end of treatment.

In order to reduce the leakage of potassium towards the deacidified permeate Pd, the permeate is maintained in the electrodialysis unit 6 at a pressure slightly greater than that of the extractor liquid E. Preferably, the pressure difference between the permeate and the extractor liquid is on the order of tenths of bars.

In addition, if the drinkable liquid to be treated L is wine, the neutralization compound N, or in particular the base added to the permeate P can cause the hydrolysis of the ethyl acetate present in the wine and hence the transformation of the ethyl acetate into ethanol and acetic acid, allowing the consequent removal of the acetic acid derived from the ethyl acetate, and hence the reduction of the concentration of ethyl acetate in the wine at the end of the treatment.

Advantageously, the process according to the present invention comprises a further operative step of reintroducing the deacidified permeate Pd obtained by the electrodialysis into the drinkable liquid to be treated L. The operative steps of the process described up to now are then repeated until the concentration of the unwanted acidic compound present in the drinkable liquid L is lower than a predetermined maximum limit concentration.

In particular, the aforesaid operative steps may only be repeated by the permeate. Otherwise, the retentate R can also be reintroduced into the first tank 2 and be made to recirculate in the plant together with the deacidified permeate Pd.

The process further comprises, at the end of the treatment, an operative step of mixing the deacidified permeate Pd with the retentate R to obtain the deacidified drinkable liquid. More in detail, as previously specified, the steps of separating, of adjusting the conductivity of the permeate P i.e. in particular possibly neutralizing, of extracting the unwanted acidic compound from the permeate through electrodialysis, and of reintroducing the deacidified permeate into the drinkable liquid to be treated L, are repeated until the concentration of the unwanted compound in the deacidified permeate Pd or in the drinkable liquid L (obtained from the mixing of the retentate R with the deacidified permeate Pd) reaches a value lower than the pre-established limit value, or until the conductivity of the deacidified permeate Pd is lower than a maximum preset threshold value. The final step of the process in any case provides for the mixing of the deacidified permeate Pd with the retentate R to obtain the deacidified drinkable liquid. Advantageously, only a fraction of the drinkable liquid—of which it is desired to reduce the content of an unwanted acidic compound—can be subjected to the process of extracting the above-described compound. The nearly complete removal of such compound from only the fraction of the drinkable liquid subjected to the extraction process is indeed sufficient for reducing the concentration of the same unwanted compound in the overall drinkable liquid, when the treated fraction of the latter is recombined with the non-treated fraction.

The finding thus conceived therefore attains the pre-established objects. Of course, in the practical achievement thereof, it can also assume forms and configurations that are different from that illustrated above, without departing from the present protective scope. In addition, all details can be substituted by technically equivalent elements and the shapes, size and materials used can be of any type in accordance with the requirements.

The invention claimed is:

1. Process for extracting at least one unwanted acidic compound from a drinkable liquid characterized in that it comprises the following operative steps:
   arranging, in a first tank (2), a drinkable liquid to be treated (L) comprising at least one unwanted acidic compound;
   conveying said drinkable liquid to be treated (L) to a membrane separation unit (3);

separating, in said membrane separation unit (3), said drinkable liquid to be treated (L) into a retentate (R) and a permeate (P), said at least one unwanted acidic compound being mainly contained in said permeate (P);

adjusting the conductivity of said permeate (P) to a minimum threshold value greater than 200 μS, susceptible to dissociate at least a fraction of said unwanted acidic compound into corresponding ions;

subsequent flowing of said permeate (P) through an electrodialysis unit (6), with extraction of at least a part of said ions, in order to obtain at least one concentrate (C), containing said ions, and at least one permeate (Pd) substantially without said ions, being deacidified from said at least one unwanted acidic compound;

mixing said permeate (Pd) with said retentate (R) to obtain a final drinkable liquid, and wherein said adjustment of the conductivity of the permeate (P) comprises
a first step of determining the conductivity of said permeate (P);
a first step of confronting the determined value with said minimum threshold value; and
a step of introducing in said permeate (P) a correspondent dose of at least one neutralization compound (N) susceptible to bring the conductivity of said permeate (P) to a value greater than said minimum threshold value.

2. Process according to claim 1, characterized in that said step of flowing said permeate (P) through said electrodialysis unit (6) envisages a second step of determining the conductivity of said permeate (P) exiting said electrodialysis unit (6), a second step of confronting the determined value with a reference value of conductivity of said permeate (P) to which a threshold value of concentration of said unwanted acidic compound corresponds, a step of recirculating said permeate (P) in said electrodyalisis unit (6) until in said confronting step the determined value is lower than said reference value.

3. Process according to claim 1, characterized in that it comprises a further operative step of reintroducing said permeate (Pd) in said drinkable liquid to be treated (L) and characterized in that at least said operative steps of conveying said drinkable liquid to be treated (L) to a membrane separation unit (3), of separating, of adjusting the conductivity of said permeate (P), of flowing said permeate (P) through an electrodialysis unit (6) with extraction of at least part of the ions derived from said at least one unwanted acidic compound from said permeate (P), and of reintroducing said permeate (Pd) in said drinkable liquid to be treated (L), are repeated until said at least one unwanted acidic compound is present in said permeate (Pd) or in said drinkable liquid (L) in a lower concentration with respect to a predetermined maximum limit concentration.

4. Process according to claim 1, characterized in that said separation is carried out through reverse osmosis.

5. Process according to claim 1, characterized in that it further comprises, before said step of introducing a correspondent dose of said at least one neutralization compound (N) in said permeate (P), the following further operative steps: determining the concentration of said at least one unwanted acidic compound in said drinkable liquid to be treated (L) or in said permeate (P); and consequently defining said dose of said at least one neutralization compound (N) that must be added to said permeate (P) in order to allow its neutralization.

6. Process according to claim 5, characterized in that the dose of said at least one neutralization compound (N) that is added to said permeate (P) is substantially equal to the dose stoichiometrically necessary for reacting with said at least one unwanted acidic compound present in said drinkable liquid to be treated (L) or in said permeate (P) in the concentration determined during said step of determining the concentration of said at least one unwanted acidic compound.

7. Process according to claim 5, characterized in that the dose of said at least one neutralization compound (N) that is added to said permeate (P) is greater than the dose stoichiometrically necessary for reacting with said at least one unwanted acidic compound present in said drinkable liquid to be treated (L) or in said permeate (P) in the concentration determined during said step of determining the concentration of said at least one unwanted acidic compound.

8. Process according to claim 1, characterized in that said neutralization compound (N) comprises a base and/or a salt.

9. Process according to claim 8, characterized in that said drinkable liquid to be treated is wine, said unwanted acidic compound is acetic acid and said at least one neutralization compound (N) comprises potassium hydroxide.

10. Process according to claim 9, characterized in that the stoichiometric ratio between said unwanted acidic compound present in said permeate (P) and said potassium hydroxide added to said permeate (P) is 1:1.5.

11. Process according to claim 1, characterized in that said step of introducing in said permeate (P) a corresponding dose of at least one neutralization compound (N) brings said permeate (P) to a pH comprised between 4 and 8.

* * * * *